(12) United States Patent
Itahashi et al.

(10) Patent No.: US 7,041,856 B2
(45) Date of Patent: May 9, 2006

(54) COUPLING CATALYST AND PROCESS USING THE SAME

(75) Inventors: Tamon Itahashi, Minoo (JP); Takashi Kamikawa, Nara (JP)

(73) Assignee: Sumitomo Chemical Company, Limited, Osaka (JP)

( * ) Notice: Subject to any disclaimer, the term of this patent is extended or adjusted under 35 U.S.C. 154(b) by 164 days.

(21) Appl. No.: 10/277,138

(22) Filed: Oct. 22, 2002

(65) Prior Publication Data

US 2003/0162950 A1 Aug. 28, 2003

(30) Foreign Application Priority Data

Oct. 23, 2001 (JP) ............................. 2001-324593

(51) Int. Cl.
- *C07C 41/30* (2006.01)
- *C07C 213/06* (2006.01)
- *C07B 37/04* (2006.01)
- *C07F 15/04* (2006.01)

(52) U.S. Cl. ...................... 568/642; 585/438; 585/469; 546/2; 546/348; 546/349; 558/378; 548/354.1; 534/598

(58) Field of Classification Search ................ 568/642; 585/469, 438; 546/348, 2, 349; 558/378; 534/598; 548/354.1
See application file for complete search history.

(56) References Cited

U.S. PATENT DOCUMENTS

| | | | |
|---|---|---|---|
| 3,326,990 A | 6/1967 | Clark | |
| 3,407,098 A | 10/1968 | Hurley et al. | |
| 3,600,419 A | 8/1971 | Franco et al. | |
| 3,642,760 A | 2/1972 | Baekelmans et al. | |
| 4,008,225 A | 2/1977 | L'Eplattenier et al. | |
| 4,016,157 A | 4/1977 | Vuitel et al. | |
| 4,725,685 A | 2/1988 | Lotsch | |
| 4,833,212 A | 5/1989 | Yamada et al. | |
| 5,563,263 A | 10/1996 | Kodadek et al. | |
| 6,043,363 A | 3/2000 | LaPointe et al. | |
| 6,200,925 B1 | 3/2001 | Ponasik, Jr. et al. | |
| 6,290,926 B1 | 9/2001 | Haenel et al. | |
| 2004/0167364 A1* | 8/2004 | Itahashi et al. ............. | 568/717 |

FOREIGN PATENT DOCUMENTS

| | | |
|---|---|---|
| DE | 24 46 543 A1 | 4/1976 |
| DE | 24 60 396 A1 | 6/1976 |
| EP | 0 366 573 | 5/1990 |
| JP | 11-180991 | 7/1999 |
| JP | 2000-336045 A | 12/2000 |
| JP | 2001-89402 A | 4/2001 |
| WO | WO 00/68252 | 11/2000 |
| WO | WO 00/68280 | 11/2000 |
| WO | WO 01/74743 A1 | 10/2001 |
| WO | WO 02/066486 A1 | 8/2002 |
| WO | WO 02/098931 | 12/2002 |
| WO | WO 03/027130 | 4/2003 |

OTHER PUBLICATIONS

O. Kovalchukova et al., "Synthesis and structure of d-metal complexes with derivatives of 9-oxypyrido[1,2a] pyrimidine-2-one. Crystal structure of 4-methyl-9-oxypyrido[1,2a] pyrimidine-2-one," Russian Journal of Coordination Chemistry (Translation of Koordinatsionnaya Khimiya) (2000), XP-002273688, abstract and structures, pp. 1-4.

R. Weiss et al., "Complex chemical behavior of pyrimidine derivatives. XIV. 1. Complex chemical behavior of purines toward cobalt(II) and nickel(II)," Monatsberichteder Deutschen Akademie der Wissenchaften zu Berlin (1971), XP-002273689, abstract and structures, pp. 1-11.

T. Schareina et al., "Combinatorial Libraries with P-Functinalized Aminopyridines: Ligands for the Preparation of Efficient C(Aryl)-C1 Activation Catalysts," Angewandte Chemie, International Edition, vol. 41, No. 9 (May 2, 2002), XP-002245409, pp. 1521-1523.

I. Fritsky et al., "An Allosteric Synthetic Catalyst: Metal Ions Tune the Activity of an Artificial Phosphodiesterase," Chemistry European Journal, vol. 7, No. 6 (2001), XP-002273678, pp. 1221-1231.

A. Afonin, "Coordination of aminoazines with bis (acetylacetonato) nickel(II) as studied by proton NMR," Koordinatsionnaya Khimiya (1989), XP-002273690, abstract and structures, pp. 1-14.

(Continued)

*Primary Examiner*—Rosalynd Keys
(74) *Attorney, Agent, or Firm*—Sughrue Mion, PLLC

(57) ABSTRACT

There are disclosed a process for producing a coupling compound of formula (1):

$$(Y—)_{(n-1)}R^1—R^2—(R^1)_{(n'-1)}, \quad (1)$$

wherein $R^1$ and $R^2$ independently represent
 a substituted or unsubstituted aryl group,
which process is characterized by reacting
 an unsaturated organic compound of formula (2):

$$n'(R^1X^1_n) \quad (2)$$

wherein n, n', and $R^1$ are the same as defined above, and
$X^1$ is the same or different and independently represents
 a leaving group and bonded with a sp2 carbon atom of $R^1$ group,
with a boron compound of formula (3):

$$m\{R^2(BX^2_2)_{n'}\} \quad (3)$$

wherein $R^2$ and n' are the same as defined above,
$X^2$ represents a hydroxy group, an alkoxy group, in the presence of a catalyst containing
 (A) a nickel compound, and
 (B) a nitrogen-containing cyclic compound, and the catalyst.

18 Claims, No Drawings

OTHER PUBLICATIONS

P. Singh et al., "Mixed Thiocyanate Complexes of Nickel(II) and M(I); M(I)= Copper(I) or Thallium(I)," Indian Journal of Chemistry, Section A: Inorganic, Physical, Theoretical & Analytical, vol. 19A (Oct. 1980), XP-009026930, pp. 994-997.

E. Alvarez et al., "Metal Complexation Reactions of Quinolone Antibiotics in a Quadrupole Ion Trap," Analytical Chemistry, vol., 69, No. 6 (Mar. 15, 1997), XP-002258144, pp. 1147-1155.

A. Stolzenberg et al., "F430 Model Chemistry. An Investigation of Nickel Complexes as Catalysts for the Reduction of Alkyl Halides and Methyl Coenzyme-M by Sodium Borohydride," Inorganic Chemistry, vol. 36 (1997), XP-002273679, pp. 593-600.

A. Gavrilova et al., "Principles of Mononucleating and Binucleating Ligand Design," Chemical Reviews, vol. 104, No. 2 (2004), XP-002273680, pp. 349-383.

Database Chemical Abstracts Service, Derwent Publications Ltd., Week 9043, XP-002273691; XP-002273705.

H. Brunner et al., "Asymmetrische Katalysen. XXIV. Cross-Coupling von 1-Phenylethylgrignard und Vinylbromid mit Ni-Katalysatoren Optisch Aktiver P/N-Liganden," Journal of Organometallic Chemistry, vol. 288, No. 3 (1985), XP009022049, pp. 359-363 (including English abstract).

A. Koppl et al., "Substituted 1-(2-pyridyl)-2-azaethene-N, N)-nickel dibromide complexes as catalyst precursors for homogeneous and heterogeneous ethylene polymerization," Journal of Molecular Catalysis A: Chemical, vol. 154 (2000), XP-001051966, pp. 45-53.

T. Schareina et al., "Dipyridylamine Ligands—Synthesis, Coordination Chemistry of the Group 10 Metals and Application of Nickel Complexes in Ethylene Oligomerization," European Journal of Inorganic Chemistry (2001), XP-002245411, pp. 2421-2426.

Database Chemical Abstracts Service, database accession No. 77:36015, XP-002273693.

A. Kelkar et al., "Carbonylation of methyl acetate to acetic anhydride using homogeneous nickel complex catalyst," Journal of Molecular Catalysis (1993), XP-002273694, abstract.

J. Cheng et al., "Screening of Optically Active Nickel Initiators for Enantioasymmetric Polymerization of γ-Benzyl Glutamate-N-Carboxyanhydride," Macromolecules (1999), XP-002273681, pp. 4745-4747.

Dictionary of Organometallic Compounds, MO—ZR, J. Buckingham, Ed. (1984), XP-002229908, 56 pages.

R. Sustmann et al., "Preparation, crystal structure and reactivity of bis(methyl acrylate)(pyridine)nickel(0)," Journal of Organometallic Chemistry, vol. 375 (Oct. 10, 1989), XP-000051789, pp. 259-264.

J. Garcia et al., "Cleavage of Carbon-Carbon Bonds in Aromatic Nitriles Using Nickel(0)," Journal of the American Chemical Society (2002), XP-002273682, pp. 9547-9555.

W. Ludwig et al., "Preparation and spectrophotometric investigation of nickel(II) complexes of substituted pyridine bases with differing microstructures," Helvetica Chemica Acta (1964), XP-009027177, pp. 1265-1279.

A. Lever, "The Magnetic Moments of Some Tetragonal Nickel Complexes," Inorganic Chemistry (1965), XP-002273683, pp. 763-764.

T. Kahn et al., "Synthesis and characterization of chromium (III), manganese(II), iron(III), cobalt(II), nickel(II), copper (II), zinc(II), mercury(II), ruthenium(III), rhodium(III), platinum(IV) and gold(III) complexes with 1-2'-pyridyl) benzothiazole-2-thione," Indian Journal of Chemistry, vol. 36A (Feb. 1997), XP-000917126, pp. 153-156.

V. Skopenko et al., "Reaction of nickel(II) perchlorate with amines in 1,2-propanediol carbonate," Ukrainskii Khimicheskii Zhurnal (Russian Edition) (1979), XP-002273695, abstract and structures, pp. 1-3.

J. Burgess, "Far infra-red spectra of 3- and 4-alkylpyridine complexes of some transition metal cations," Spectrochimica Acta, Part A: Molecular and Biomolecular Spectroscopy (1968), XP-009027154, pp. 277-283.

C. Janiak et al., "Co-ordination engineering: when can one speak of an "understanding"? Case study of the multidentate ligand 2,2'-dimethyl-4,4'-bipyrimidine," Journal of the Chemical Society, Dalton Transactions (1999), XP-002273684, pp. 3121-3131.

R. Acevedo-Chavez et al., "Transition metal compounds of the purinic isomer allopurinol. Part 1," Transition Metal Chemistry (1990), XP-002273696, abstract and structures, pp. 1-4.

V. Dorokhov et al., "Synthesis of ketene animals from cyclic .beta.-diketones and cyanamides using nickel acetate," Izvestiya Akademii Nauk SSSR, Seriya Khimicheskaya (1989), XP-002273697, abstract and structures, pp. 1-2.

N. Saha et al., "Metal complexes of pyrimidine-derived ligands—IV. Synthesis, characterization and coordinating properties of two guanidine pyrimidines: nickel(II) complexes with 2-guanidino-4,6-dimethylpyrimidine and 2-phenylguanidino-4,6-dimethylpyrimidine—potential ligands of biological interest," Polyhedron (1984), abstract and structures, pp. 1-4.

N. Saha et al., "Metal complexes of pyrimidine-derived ligands. I. Nickel(II) complexes of 2-hydrazino-4,6-dimethyl pyrimidine," Journal of Inorganic and Nuclear Chemistry (1977), XP-002273699, abstract and structures, pp. 1-5.

M. Tskitishvili et al., "Complex compounds of the transition metals with sulfanilamides and monoethanolamine," Bulletin of the Georgian Academy of Sciences (2000), XP-002273700, abstract and structures pp. 1-7.

C. Campbell et al., "Nickel(II) meso-Tetraphenyl-Homoporphyrins, -secochlorins, and -chlorphin: Control of Redox Chemistry by Macrocycle Rigidity," Journal of the American Chemical Society (2000), XP-002273685, pp. 6679-6685.

G. Lahiri et al., "F430 Model Chemistry. Evidence for Alkyl- and Hydrido-Nickel Intermediates in the Reactions of the Nickel(I) Octaethylisobacteriochlorin Anion," Inorganic Chemistry (1993), XP-002273686, pp. 4409-4413.

R. Saalfrank et al., "Coordination polymers. 8. Synthesis, reactivity and structure of cobalt semicorrinate complexes," Zeitschrift fuer Naturforschung, B: Chemical Sciences (1994), XP-002273701, abstract and structures, pp. 1-4.

Y. Murakami et al., Transition Metal Complexes of Pyrrole Pigments. IV. Electronic and Vibrational Spectra of Cobalt (II), Nickel(II), and Copper(II) Complexes of Some Substituted Dipyrromethenes, Inorganic Chemistry, vol. 10, No. 8 (1971), XP-002273687, pp. 1728-1734.

J. Ferguson et al, "Properties of transition-metal complexes of dipyrromethenes. I. The spectra and magnetic moments of some nickel(II) complexes," Journal of the Chemical Society [Section] A: Inorganic, Physical, Theoretical (1966), XP-002273702, abstract and structures, pp. 1-7.

Y. Ustynyuk et al, "Interactoin of nickelocene with benzal anilines," Journal of Organometallic Chemistry (1971), XP-002273703, abstract and structure, pp. 1-2.

E. Diamantopoulou et al, "Synthetic and structural chemistry of nickel(II)/1-methylbenzotriazole complexes," Polyhedron (1994), XP-002273704, abstract, 1 page.

D. Goodgame et al, "Spectroscopic Studies of Substituted Imidazole Complexes. II. N-methylimidazole Complexes of Divalent Cobalt, Nickel, Copper and Zinc", Inorganica Chimica Acta, vol. 3, Sep. 1969, pp. 406-410.

H. Carlsson et al., "Hydrolytically Active Tetranuclear Nickel Complexes with Structural Resemblance to the Active Site of Urease", Inorg. Chemistry 2002, (XP-002263170), 41, pp. 4981-4983.

J. Brown et al., "Preparation, Characterization, and Thermal Properties of Controllable Metal-Imidazole Complex Curing Agents for Epoxy Resins", Journal of Applied Polymer Science, vol 75, 2000, (XP-002263171), pp. 201-217.

S. Yamazaki et al., "Nickel-catalyzed epoxidation of olefins with sodium hypochlorite (NaOC1)", XP-002263179, pp. 1-2.

D. Batyr et al., "Effect of structural features of adducts of azoles to 3d-element bis(.beta.-diketonates) on the thermal oxidation rate of oligodienes with functional groups", XP-002263180, pp. 1-2.

K. Fujita et al., "Novel monoanionic tripodal ligands: methylbis(1-methylimidazol-2-yl) (pyrazol-1-yl)borate (= [MeB(Im$^{N-Me}$)$_2$(Pz$^R$)]). Synthesis and structural characterization of their nickel complexes and carboxylate shift from nickel to boron", J. Chem. Soc., Dalton Trans., 2000, XP-002263172, pp. 117-120.

F. Stephenns et al., "Studies on macrocyclic complexes derived form vic-dioximes. Part VIII. Bis (difluoroboronglyoximato) nickel (II) complexes and their reactions with nitorogenous bases", XP002263181, pp. 1-2.

P. Koningsbruggen et al., "Crystal structure and physical properties of the new linear chain compound [Cu(1,2-bis (tetrazol-1-yl)ethane)$_3$](ClO$_4$)$_2$", Inorganica Chimica Acta 326, 2001, (XP-002263173), pp. 101-105.

M.Z. Wisniewski et al., "Pentamethylenetetrazole complexes of Co (II), Ni (II) and Cu (II)", XP-002263182, pp. 1-2.

A. Stassen et al., "Physical properties of the spin-crossover compound hexakis(1-methyltetrazole-N$^4$)iron(II) triflate, steady state and relaxation studies, X-ray structure of the isomorphic Ni(II) compound", Polyhedron 20, 2001, (XP-002263174), pp. 1699-1707.

P. Koniingsbruggen et al., "A new 3-D polymeric spin transition compound: [tris(1,4-bis-(tetrazol-1-yl)butance-N1,N1')iron(II)] bis(perchlorate)", J. Chem. Soc., Dalton Trans., 2001, (XP-002263175), pp. 466-471.

L. Lavrenova et al., "Complex compounds of cobalt (II), nickel (II) and copper (II) with 1-phenyltetrazole and 1-ethyltetrazole", XP-002263183, pp. 1-2.

L. Lavrenova et al., "Complexes of Co (II), Ni (II), and Cu (II) with 1-vinyltetrazole and 1-allyltetrazole", XP-002263814, pp. 1-5.

T. Buchen et al., "Thermal and Light-Induced Spin Transition in the High-and Low-Temperature Structure of [Fe$_{0.35}$Ni$_{0.65}$(mtz)$_6$](ClO$_4$)$_2$", Inorg. Chem. 1996, 35, (XP-002263176), pp. 155-161.

A. Bogatikov et al., "Complex nitrate compounds with 1- and 2-ethyltetrazoles", XP-002263185, pp. 1-2.

V. Sinditskii et al., "Synthesis and spectroscopic studies on nickel (II), cobalt (II) and copper (II) complexes of tetrazolyl-1-acethydrazide. Crystal structure of [Cu(TH-1)2](ClO4)2", XP-002263186, pp. 1-4.

P. Franke et al., "Tetrazoles as ligands, Part III. Transition metal complexes of 1—alkyltetrazoles", XP-002263187, pp. 1-5.

B. Lorant, "Analytical application and derivatographic characterization of metal-thiocyanate complexes linked with aminoazophene, dimethyl aminoazophene, and pentamethylene tetrazoleas ligands", XP-002263188, pp. 1-2.

H. Hoberg et al., "A 1-oxa-2-nickela-5-cyclopentanone from ethane and carbon dioxide; preparation, structure and reactivity", XP-002263189, pp. 1-2.

N. Saito et al., "Preparation of benzimidazole compounds, azobenzimiazole compounds, and their chelates", XP-002263190, pp. 1-2.

A. Watson et al., "Chiral heterocyclic ligands. VIII. Syntheses and complexes of new chelating ligands derived from camphor", XP-002263191, pp. 1-4.

B. Mercimek et al., "The synthesis and Ni (II), Co (II), Cu (II), Zn (II), Cd (II), and Hg (II) complexes of bis (.DELTA. 2-2- pyrimidinyl), -6,6 -dioxime dihydrochloride", XP-002263192, pp. 1-3.

T. La et al., "Solution Chemistry and Crystal Structure of Nickel Tetrakis (2,3,5,6-tetrafluoro-N,N, N-trimethyl-4aniliniumyl)porphyrin Trifluoromethanesulfonate (NiTF$_4$TMAP(CF$_3$SO$_3$)$_4$)", Inorg. Chem., 1995, (XP-002263177), pp. 5632-5640.

M. Elder et al., "Reactions of Coordinated Ligands. XII. The Synthesis of o-Benzylene-2,1-benzimidazole in the Presence of Nickel (II) Ions, and a Study of Some of Its Metal Complexes", Inorganic Chemistry, (XP-002263178), pp. 74-77.

N. Leadbeater et al., "Suzuki Aryl Coupling Mediated by Phosphine-Free Nickel Cp,plexes", Tetrahedron 55, (1999), pp. 11889-11894 with Abstract.

D.M.L. Goodgame et al., "Spectroscopic Studies of Substituted Imidazole Complexes II N-methylimidazole Complexes of Divalent Cobalt, Nickel, Cooper and Zinc", Inorganica Chimica Acta [3:3] Sep. 1969, pp. 406-410.

S. Saito et al., Synthesis of Biaryls via a Nickel (0)-Catalyzed Cross-Coupling Reaction of Chloroarenes with Arylboronic Acids, J. Org. Chem. 62, (1997), pp. 8024-8030.

Y. Kyokaishi, "Synthesis of Neutral π-Allypalladium Complexes having Bisnitrogen Ligands and Palladuim-Catalyzed Cyclopropanation of Ketene Silyl Acetals with Allylic Acetatas", vol. 58, (Aug. 2000), pp. 736-744 with Abstract and a copy of translation of footnote 10 is attached.

* cited by examiner

COUPLING CATALYST AND PROCESS USING THE SAME

BACKGROUND OF THE INVENTION

The present invention relates to a coupling catalyst comprising a nickel compound and a nitrogen-containing cyclic compound and a process for producing a coupling compound by reacting an unsaturated organic compound and boron compound using the catalyst.

There has been a growing demand for biaryl type coupling compounds as production intermediates for producing pharmaceuticals, agrochemicals, liquid crystal material, and organic electronic luminescence material. Suzuki coupling reaction comprising reacting a boron compound with an aryl halide compound by using a nickel catalyst can be mentioned as a versatile process for producing biaryl type coupling compounds. In the reaction, phosphine compounds have been exclusively used as a ligand of the nickel catalyst, and a catalyst using an amine compound as the ligand in the reaction were only rarely known for a catalyst using 2,2'-bipyridyl or triethylamine since it has been well known in the art that an amine compound having a nitrogen atom, which is an element of Group 15 of the Periodic Table of Elements as the phosphrous atom of a phosphine, is inferior to phosphine ligand in their ability to coordinate with a metal atom (Yukigosei Kagaku Kyokaishi, vol. 58, August, 2000, p. 736–744, Tetrahedron Vol. 55, p. 1889,1993). The coupling reaction using 2,2'-bipyridyl or triethylamine were not always satisfactory in that the reaction using the catalyst containing 2,2'-bipyridyl ligand is accompanied by a significant amount of byproducts and reaction activity of the catalyst containing triethylamine was limited.

Nickel complexes prepared from a hydrate of nickel chloride, bromide or iodide or nickel nitrate, and 1-methylimidazole or 1,2-dimethylimidazole in a mixture of ethanol and 2,2-dimethoxypropane were known, however, catalytic activity of these compounds were not known nor suggested (Inorganic Chimica Acta., pp. 406–410 September, 1969).

SUMMARY OF THE INVENTION

According to the present invention, a coupling reaction can be carried out with good selectivity by using a catalyst comprising, as components, a readily available and inexpensive nitrogen-containing cyclic compound and a nickel compound.

The present invention provides:
1. a process for producing a coupling compound of formula (1):

$$(Y-)_{(n-1)}R^1-R^2-(R^1)_{(n'-1)} \quad (1)$$

wherein $R^1$ and $R^2$ independently represent
a substituted or unsubstituted aryl group,
a substituted or unsubstituted heteroaryl group, or
a substituted or unsubstituted linear, branched or cyclic alkenyl group,
n and n' independently represent an integer of 1 or 2, provided that n and n' do not simultaneously represent 2, and when n=2, Y represents $R^2$, or $X^1$ as defined below, which process comprises reacting an unsaturated organic compound of formula (2):

$$n'(R^1X^1_n) \quad (2)$$

wherein n, n', and $R^1$ are the same as defined above, and $X^1$ is the same or different and independently represents a leaving group and bonded with a sp2 carbon atom of $R^1$ group, with a boron compound of formula (3):

$$m\{R^2(BX^2_2)_{n'}\} \quad (3)$$

wherein $R^2$ and n' are the same as defined above,
$X^2$ represents a hydroxy group, an alkoxy group, or $X^2$ groups are bonded at their terminals to form an alkylenedioxy group or an arylenedioxy group, and
m represents an integer of 1 or 2,
provided that the boron atom is bonded with a sp2 carbon atom of $R^2$ group, and
m≦n, wherein n is the same as defined in connection with formula (1) above, or
a cyclic anhydride trimer thereof of formula:(—O—B($R^2$)—)$_3$, wherein $R^2$ is the same as defined above,
in the presence of a catalyst comprising
(A) a nickel compound, and
(B) a nitrogen-containing cyclic compound selected from:
  (a) a nitrogen-containing cyclic compound of formula (I):

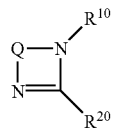

wherein Q represents
    a substituted or unsubstituted alkylene group,
    a substituted or unsubstituted alkenylene group,
    a substituted or unsubstituted 1,2-phenylene group,
    a substituted or unsubstituted 1,8-naphthylene group, or
    —N=N— group,
  $R^{10}$ represents
    a substituted or unsubstituted hydrocarbon group, and
  $R^{20}$ represents
    a hydrogen atom, a substituted or unsubstituted hydrocarbon group,
    alternatively, $R^{10}$ and $R^{20}$ are bonded at their terminals to form a substituted or unsubstituted alkylene, or alkenylene group,
  (b) a substituted or unsubstituted pyridine or fused ring compound thereof of which conjugated acid has pKa of 5 or more,
  (c) a substituted pyrimidine or substituted or unsubstituted fused pyrimidine compound of which conjugate acid has pKa of 3 or more,
  (d) an enamine compound obtainable from a cyclic ketone compound and a cyclic secondary amine compound,
  (e) a substituted or unsubstituted 2H-pyrrole, 3,4-dihydro-2H-pyrrole, 3H-pyrrole or fused ring compound thereof, or
  (f) a substituted or unsubstituted N-hydrocarbyl-1,2,3-triazole or fused ring compound thereof; and
2. a catalyst composition:
1) comprising (A) the nickel compound, (B) the nitrogen-containing cyclic compound as defined above, and a solvent, provided that said solvent is not a solvent consisting of ethanol and 2,2-dimethoxypropane, 2) comprising (A) the nickel compound, (B) the nitrogen-containing cyclic compound as defined above, and a solvent consisting essentially of an aprotic organic solvent,
3) comprising (A1) a zero valent nickel compound, and (B) the nitrogen-containing cyclic compound as defined above,
4) obtainable by reacting (i) (A2) a divalent nickel compound, with (B) the nitrogen-containing cyclic compound as defined above, in the presence of a reducing agent, or
5) comprising (A) the nickel compound, and (B) the nitrogen-containing cyclic compound as defined above, with the proviso that said nitrogen-containing cyclic compound is not 1-methylimidazole nor 1,2-dimethylimidazole when said nickel compound is a hydrate of nickel chloride, bromide or iodide or nickel nitrate.

DETAILED DESCRIPTION OF THE INVENTION

A description will be made to the nickel compound.

Examples of the nickel compound that may be used in the present production process as a component of the catalyst include, for example, a divalent or zero valent nickel compound.

Examples of the divalent nickel compound include, for example, a nickel salt, a complex salt of a divalent nickel, nickel hydroxide, a π-complex compound of divalent or zero valent nickel.

Examples of the nickel salt include, for example, a salt of nickel and inorganic or organic acid. Specific examples of the salt of nickel and inorganic acid include, for example, a nickel halide such as nickel (II) chloride, nickel (II) bromide, nickel(II) iodide or the like, nickel(II) nitrate, nickel (II) sulfate, nickel(II) ammonium sulfate, nickel(II) sulfamidate, nickel(II) hypophosphate. Preferred are the nickel halide and nickel nitrate.

Examples of the salt of nickel and organic acid include, for example, nickel(II) acetate, nickel(II) stearate, nickel (II) cyclohexanebutyrate, nickel (II) citrate, nickel (II) naphthenate, nickel(II) formate and the like. Preferred is nickel(II) acetate.

Examples of the complex salt of divalent nickel include, for example, an amine complex of the divalent nickel compound such as hexaaminenickel(II) chloride, or hexaaminenickel(II) iodide, and acetylacetone complex of nickel such as nickel (II) acetylacetonate or the like.

Examples of the nickel hydroxide include, for example, nickel(II) hydroxie.

Examples of the π-complex compound of divalent nickel include, for example, bis($\eta^3$-allyl)nickel(II) and bis($\eta$-cyclopentadienyl)nickel(II), and allylnickel chloride diner and the like.

Examples of the π-complex compound of zero valent nickel include, for example, bis(1,5-cyclooctadiene)nickel (0), nickel carbonyl(0) and the like.

These nickel compounds may be anhydrous or hydrated. Preferred nickel compounds are nickel(II) chloride, nickel (II) bromide, nickel(II) iodide, nickel(II) nitrate, bis(1,5-cyclooctadiene)nickel, and nickel(II) acetate.

The amount of the nickel compound may be a catalytic amount and is typically in an amount of 0.00001 mol to 1 mole, preferably 0.2 mol or less per mol of the unsaturated organic compound of formula (2).

Next, a description will be made to the nitrogen-containing cyclic compound that may be used, as a ligand or a component, of the catalyst of the present invention.

The hydrocarbon group represented by $R^{10}$ or $R^{20}$ encompasses saturated and unsaturated hydrocarbon groups.

Examples of the substituted or unsubstituted hydrocarbon group represented by $R^{10}$ or $R^{20}$ include, for example, a linear, or branched, C1–10 alkyl group such as methyl, ethyl, propyl, butyl, pentyl, hexyl, heptyl, octyl, nonyl, decyl, and a C4–10 cyclic alkyl group such as cyclobutyl, cyclopentyl, cyclohexyl, cycloheptyl, cyclooctyl or cyclodecyl group, and the like.

Examples of the substituted or unsubstituted hydrocarbon group represented by $R^{10}$ or $R^{20}$ include, for example, a linear, or branched C2–10 alkenyl group such as vinyl, propenyl, butenyl, hexenyl, heptenyl, octenyl, nonenyl, decenyl, and a C5–10 cycloalkenyl group such as cyclopentenyl, cyclohexeneyl, cyclooctadienyl group, and a C6–16 aryl group such as phenyl, naphthy, anthracenyl, phenanthryl, indenyl, fulorenyl, or pyrenyl group and the like.

Examples of the substituted or unsubstituted alkylene group represented by Q, or formed by $R^{10}$ and $R^{20}$ include, for example, a C3–6 alkylene group such as trimethylene, tetramethylene, pentamethylene, hexamethylene or the like.

Examples of the compound of formula (I), wherein Q represents an alkylene group and $R^{10}$ and $R^{20}$ groups also form an alkylene group, include, for example, 1.8-diazabicyclo[5.4.0]-7-undecene, 1,2-Dimethyl-1,4,5,6-tetrahydropyrimidine, 1.5-diazabicylo[4.3.0]non-5-ene and the like.

Examples of the substituted or unsubstituted alkenylene group represented by Q, or formed by $R^{10}$ and $R^{20}$ include, for example, a C2–5 alkeneylene group such as ethylene, propenylene, butadienyl, butenylene, or pentenylene group, and the like. Specific examples of the compound of formula (I), wherein Q, or $R^{10}$ and $R^{20}$ forms the alkenylene group include, for example, 1-methylimidazole, 2-ethyl-4-methylimidazole, 1,2-dimethylimidazole, 1,2-dicyclohexylimidazole, N-benzylimidazole, 1-vinylimidazole, 1-phenylimidazole, imidazo[1.2-a]pyridine (pKa: 4.9), 1-methylhistidine and the like.

Examples of the compound of formula (I) wherein Q is a substituted or unsubstituted 1,2-phenylene group, include, for example, a substituted or unsubstituted N-hydrocarbyl-benzimidazole, and specific examples thereof include, for example, N-methylbenzimidazole.

Examples of the compound of formula (I) wherein Q is a substituted or unsubstituted 1,8-naphthylene group include, for example, N-hydrocarbylperimidine compound such as N-methylperimidine.

The hydrocarbyl group referred to in the present description also includes those groups as specified above for the hydrocarbon group represented by $R^{10}$ or $R^{20}$.

Examples of the compound of formula (I) wherein Q is —N=N— group include, for example, N-hydrocarbyltetrazole compound such as 1,5-pentamethylenetetrazole.

Examples of the substituted or unsubstituted pyridine or fused ring compound thereof (e.g. with a benzene ring or the like) of which conjugated acid has pKa of 5 or more include, for example, pyridine (pKa of its conjugate acid: 5.4, hereinafter referred to merely as "pKa"), quinoline (pKa: 5.0), isoquinoline (pKa: 5.37), 4-vinylpyridine (pKa: 5.39), N-methyl-β-carboline (pKa: 5.47), acrydine (pKa: 5.50), β-picoline (pKa: 5.52), 3,5-lutidine (pKa: 5.81), 4 isopropylpyridine (pKa: 6.0), N,N-dimethylaminopyridine (pKa: 9.7) and the like. Among said compounds, the compounds of which conjugated acid has a pKa value of 6 or more are preferred, more preferred are the compounds of which conjugated acid has a pKa value of 7 or more, yet more preferred are the compounds of which conjugated acid has a pKa value of 9 or more.

Said pKa value of the conjugated acid of the nitrogen-containing cyclic compounds of groups (b) and (c) can be calculated by a commercially available software (Product of LA Systems, ACD/pKa (version 1.0), and an updated version may be relied on, if appropriate) and the pKa values recited in the present specification are calculated by the software. As for the software, a web-site, http://acdlabs.com. can be referred to. ACD/pKa is a program that calculates acid-base ionization constants (pKa values) under 25° C. and zero ionic strength in aqueous solutions for a given organic structure. Each calculation is provided with both its ±95% confidence limits and a detailed report of how it has been carried out, including Hammett-type equation(s), substituent constants, and literature references where available. The accuracy of calculations is usually better than ±0.2 pKa units except for very complex structures or poorly-characterized substituents, where the accuracy is usually better than ±0.5 pKa units. In order to achieve this accuracy, ACD/pKa DB uses its own internal databases and algorithms.

Examples of the substituted pyrimidine of which conjugate acid has pKa of 3 or more include, for example, a substituted or unsubstituted fused ring compound of pyrimidine, and specific examples thereof include, for example, 4,6-dimethylpyrimidine (pKa: 3.0), quinazoline (pKa: 3.4), pteridine (pKa: 3.75).

Examples of the cyclic ketone compound that may be used to obtain the enamine compound include, for example, a 5 to 10 membered aliphatic ketone such as cyclopentanone, cyclohexanone, cycloheptanone, cyclooctanone, cyclononanone, cyclodecanone or the like.

Examples of the cyclic secondary amine compound that may be used to obtain the enamine compound include, for example, a C4–6 alkyleneimine such as pyrrolidine, 3-dimethylaminopyrrolidine, piperidine, hexamethyleneimine, or heptametyleneimine, of which alkylene group may be substituted, for example, with an alkyl group, a dialkyl amino group or other substituent groups as exemplified below for the nitrogen-containing cyclic compound of groups (a), (b), (c), (e) and (f). Specific examples of the eanmine compound include, for example, an enamine obtainable from pyrrolidine and cyclohexanone.

Examples of the substituted or unsubstituted 2H-pyrrole, 3,4-dihydro-2H-pyrrole, or 3H-pyrrole or fused ring compound thereof include, for example, 2H-pyrrole, 3,4-dihydro-2H-pyrrole, 2-methyl-1-pyrroline, 1-methylpyrroline, 3H-pyrrole, 3H-indole, 4aH-carbazole and the like.

Examples of the substituted or unsubstituted N-hydrocarbyl-1,2,3-triazole or fused ring compound thereof include, for example, N-methylbenzotriazole, 1-methyl-1,2,3-triazole, 2-methyl-1,2,3-triazole or the like.

The substituted nitrogen-containing cyclic group as recited (a) to (f) above may be substituted with at least one group selected from:
 an alkyl group such as C1–10 alkyl group as described above,
 an alkoxy group such as C1–10 alkoxy group (e.g. methoxy, ethoxy, propoxy, butoxy, pentyloxy, hexyloxy, heptyloxy, octyloxy, nonyloxy, and decyloxy groups),
 an aryl group as described above,
 an aralkyl group (e.g. an alkyl group such as C1–10 alkyl group, which alkyl is substituted with the aryl group as specified above, such as benzyl, phenethyl, naphthylmethyl, naphthylethyl or the like),
 an alkenyl group (e.g. C2–10 linear, branched or cyclic alkenyl group as described above), or
 a dialkyl amino group (e.g. an amino group substituted with two linear, or branched C1–10 alkyl group or a C3–10 cycloalkyl groups as described above, or a C3–6 alkylene group, and specific examples thereof include, for example, a dimethylamino, diethylamino, pyrrolidino, or piperidino group).

Preferred is the nitrogen-containing cyclic compound recited under item (a) above among the groups.

Preferred specific compounds are N-methylimidazole, N,N-dimethylaminopyridine, and 1,8-diazabicylo[5.4.0]-7-undecene.

The nitrogen-containing cyclic compound may be supported on a resin that cannot be dissolved in a reaction solvent, and can be used as a heterogeneous catalyst. Examples thereof include N,N-dimethylaminopyridine supported on a polystyrene.

The nitrogen-containing cyclic compound (B) can used in a catalytic amount and is typically used in an amount of 0.1 mol or more, preferably, 1 to 10 moles per 1 gram atom of a nickel atom of the nickel compound. The nitrogen-containing cyclic compound (B) may be used in an excess amount as a solvent when the compound (B) is a liquid at the reaction temperature.

When the unsaturated organic compound of formula (1) or the boron compound of formula (2) contains chemical structures as featured under (a) to (f) above of the nitrogen-containing cyclic compound, they may be served as the present catalyst component.

The nickel compound may be used in the coupling reaction in a form of a solution in which it is completely dissolved or in a form of suspension, or it may be supported on a support such as carbon, silica, or alumina.

The catalyst of the present invention may be prepared prior to the coupling reaction, for example, as a catalyst preparation composition containing the nickel compound (A) and the nitrogen-containing cyclic compound (B), and optionally a suitable solvent. Alternatively, the nickel compound (A) and the nitrogen-containing cyclic compound (B) maybe independently or simultaneously added to a reaction mixture containing the unsaturated organic compound of formula (2) and the boron compound of formula (3).

Examples of the catalyst that may be suitably prepared from the components (A) and (B) include, for example, the catalyst compositions 1) to 5) described above.

Examples of the solvent that may be suitably used for preparing the catalyst composition 1) include water, and the same organic solvent including an aprotic organic solvent such as an aprotic polar solvent, an ether, an aromatic hydrocarbon, and an aliphatic hydrocarbon as exemplified below as the solvent for the coupling reaction.

Examples of the reducing agent that may be suitably used to prepare the catalyst composition 4) recited above include, for example, sodium borohydride, lithium aluminum hydride, sodium hydride, diisobutyl aluminum hydride, alkyl Grignard reagent, alkyl lithium (e.g. butyl lithium), zinc metal. Preferred are the alkyl Grignard reagent and alkyl lithium, and more preferred is butyl lithium.

The (A) divalent nickel compound, the (B) nitrogen-containing cyclic compound, and the reducing agent may be contacted, preferably in an inert organic solvent, and the components (A), (B) and the reducing agent may be optionally mixed with other(s), but the catalyst may be typically obtainable by reacting (i) (A2) a divalent nickel compound, with (B) a nitrogen-containing cyclic compound as defined above, and (ii) reacting the resulting mixture with the reducing agent.

Examples of the inert organic solvent include an ether solvent, a hydrocarbon solvent, a reaction solvent that may be suitably used for the coupling reaction as described below, and a mixture thereof. Preferred solvents are the ether and hydrocarbon solvent.

The present coupling reaction includes following reactions:

when n=n'=1, $$R^1-X^1 + R^2-(BX^2{}_2) \longrightarrow R^1-R^2, \quad (Eq. 1)$$
$$(2a) \qquad (3a) \qquad\qquad (1a)$$

when n=2, n'=1 and m=1, $$X^1-R^1-X^1 + R^2-(BX^2{}_2) \longrightarrow X^1-R^1-R^2, \quad (Eq. 2)$$
$$(2b) \qquad\quad (3b) \qquad\qquad (1b)$$

when n=2, n'=1, and m=2, $$X^1-R^1-X^1 + 2\{R^2-(BX^2{}_2)\} \longrightarrow R^2-R^1-R^2, \text{ and} \quad (Eq. 3)$$
$$(2c) \qquad\quad (3c) \qquad\qquad (1c)$$

when n=1, and n'=2, $$2R^1-X^1 + (BX^2{}_2)-R^2-(BX^2{}_2) \longrightarrow R^1-R^2-R^1. \quad (Eq. 4)$$
$$(2d) \qquad\quad (3d) \qquad\qquad (1d)$$

In the coupling reaction of the present invention, a carbon-carbon bond is selectively formed between two sp2 carbon atoms to which the leaving group and the boron atom are respectively bonded to produce a desired coupling product.

A description will be made to the unsaturated organic compound of formula (2) that may be suitable used in the present coupling reaction.

Examples of the leaving group represented by $X^1$ include a halogen atom such as chlorine, bromine, or iodine, a sulfonate group such as methanesulfonyloxy, trifluoromethanesulfonyloxy, or p-toluenesulfonyloxy group, and a diazonium salt.

Examples of the substituted or unsubstituted aryl group represented by $R^1$ include, for example, substituted or unsubstituted C6–16 aryl group such as phenyl, naphthyl, anthracenyl, phenanthryl, indenyl, fluorenyl or pyrenyl group.

Examples of the substituted or unsubstituted heteroaryl group include, for example, a pyridyl, quinazolyl, quinolyl, pyrimidyl, furyl, thienyl, pyrrolyl, imidazolyl, or tetrazolyl group.

Preferred examples of the substituted or unsubstituted aryl group include a compound of formula (4):

$$\left[(R^3)_k-\underset{X^1}{\bigcirc}-(X^1)_l\right] \quad (4)$$

wherein $R^3$ is the same or different and each independently represents a substituent group, or $R^3$ groups on adjacent benzene carbon atoms, together with the benzene ring to which they are bonded, optionally form a ortho-fused, or ortho- and peri-fused aromatic ring compound (e.g. naphthyl, anthracenyl, phenanthryl, indenyl, fluorenyl or pyrenyl group), $X^1$ represents a leaving group bonded with a sp2 carbon atom, l is an integer of 0 or 1, and k is an integer of 0 to 5, provided that at least one ortho-position of the leaving group is a hydrogen atom or a common carbon atom of the fused aromatic ring compound.

Examples of the substituted or unsubstituted alkenyl group represented by $R^1$ include, for example, a substituted or unsubstituted linear, or branched C2–10 alkenyl group and C5–10 cyclic alkenyl group.

Specific examples thereof include, for example, 5- to 10-membered cycloalkenyl group having at least one double bond and may be substituted with an oxo group such as cyclohexenyl, cyclopentenyl, 1,4-benzoquinonyl, 6-oxocyclohexe-1-enyl, or 5'-oxocyclopent-1-enyl group.

Examples of the substituent group with which $R^1$ group may be substituted or the substituents represented by $R^3$ or $R^5$ below include, for example, a linear, branched or cyclic alkyl group (e.g, C1–10alkyl group as exemplified above) such as methyl, ethyl, i-propyl, cyclohexyl, or the like, a haloalkyl group such as trifluoromethyl group, a fluorine atom, an alkoxy group (e.g. C1–C10alkoxy group as exemplified above) such as methoxy, ethoxy, t-butoxy, pentyloxy, hexyloxy, heptyloxy, octyloxy, nonyloxy, or decyloxy group, an aryloxy group such as phenoxy or the like, a hydroxy group, an arylthio group such as phenylthio group, or the like, a cyano group, a nitro group, an amino group which may be substituted with an alkyl group or groups such as an amino, dimethylamino, pyrrolidino, piperlidino, or cyclohexylamino group, or the like, a carbamate group which may be substituted with an alkyl group (e.g. C1–10 alkyl as exemplified above) such as t-butylcarbamate, or methylcarbamate, a sulfonamide group which may be substituted with an alkyl, haloalkyl, or aryl group such as benzenesulfonamide, or methanesulfonamide, an imino group, an imido group such as phthalimide, a formyl group, a carboxyl group, an alkoxycarbonyl group, in which the alkoxy include the C1–10 alkoxy group as exemplified above, such as methoxycarbonyl group, aryloxycarbonyl group such as p-methoxyphenoxycarbonyl group, a substituted or unsubstituted carbamoyl group such as carbamoyl or N-hydrocarbyl substituted carbamoyl (e.g. N-phenylcarbamoyl group), a heteroaryl group such as pyridyl, quinazolyl, pyrimidyl, furyl, thienyl, pyrrolyl, or imidazolyl group, and an aryl group such as phenyl or naphthyl group.

Specific examples of the unsaturated organic compound of formula (1) include, for example, bromobenzene, o-bromotoluene, p-t-butylbromobenzene, 3,5-dimethylbromobenzene, 2-hydroxyethylbromobenzene, 4-cyclohexylbromobenzene, 3-bromobenzotrifluoride, beta-bromostyrene, 3-bromo-4-chlorobenzotrifluoride, 2-naphthylbromide, 9,10-dibromoanthracene, 9-bromoanthracene, 2-t-butyl-9,10-dibromoanthracene, 1,3-dibromobenzene, m-methoxybromobenzene, 4-bromobenzaldehyde, 1,4-dibromo-2-fluorobenzene, methyl 2-bromophenylacetate, methyl 3-bromophenylacetate, ethyl 4-bromophenylacetate, methyl 3-bromocinnamate, methyl 5-bromosalycylate, 4-bromobenzamide, 4-bromobenzonitrile, 9-bromophenanthrene, 2-bromofluorrene, 5-bromoindanone, 2,7-dibromofluorene, 2,7-dibromo-9,9-dinonylfluorene, 2,7-dibromo-9,9-dioctylfluorene, 6-bromo-2-naphthol, 4,4'-dibromobiphenyl, 2-bromopyridine, 2-bromofurane, 3-bromofurane, 2-bromothiophene, 5-bromouracil, 8-bromoquinoline, 4-bromoisoquinoline, 1-benzyl-5-bromotetrazole, chlorobenzene, 2-chlrolotoluene, 3-chlorotoluene, 4-chlorotoluene, 2-chloroacetophenone, 4-chloroacetophenone, p-t-butylchlorobenzene, 3,5-dimethylchlorobenzene, 4-cyclohexylchlorobenzene, 2-chloro-4-fluorotoluene, methyl 1-chloro-4-nitrobenzene, 2-chlorophenylacetate, methyl 3-chlorophenylacetate, methyl 4-chlorophenylacetate, 3-chlorobenzophenone, 4-chloro-1-naphthol, 4-chloroaniline, 4-chloro-N,N'-dimethylaniline, 4-chloro-N,N'-dipohenylaniline, 5-chloro-N,N'-dimethylaniline, 5-chloro-2-methoxyaniline, 4-chlorobenzoic acid, methyl 3-chlorobenzoate, phenyl 2-chlorobenzoate, 2-chlorophenylacetoamide, 4-chlorophenylacetamide, 2-chlorobenzylcyanide, 2-chloronaphthalene, 9,10-dichloroanthracene, 9-chloroanthracene, 1,3-dichlorobenzene, 9-chloroanthracene, 1,3-dichlorobenzene, o-methoxychlorobenzene, m-methoxychlorobenzene, p-methoxychlorobenzene, 3,5-dimethoxychlorobenzene, 3-chlorobenzonitrile, 2,7-dichloro-9-fluorenone, 2-chloro-3-morpholino-1,4-naphthoquinone, 3-chlorobenzaldehyde, 4,4-dichloro-2-fluorobenzene, 2-chloropyridine, 2-chloro-6-trifluoromethylpyridine, 1-(3-chlorophenyl)-3-methyl-2-pyrazoline-5-one, 3-chlorothiophene, 5-chloro-1-methylimidazole, 5-chloro-1-phenyl-1H-tetrazole, 4-chloroindole, 2-chlorobenzimidazole, 8-chloro-5-methoxyquinoline, 2,6-dichloropyridine, 3,5-dichloropyridine, 6-chloropurine, 2,4-dichloropyrimidine, iodobenzene, 2-iodotoluene, p-t-butyliodobenzene, 3,5-dimethyliodobenzene, 4-iodoacetophenone, 2-iodobenzoic acid, 2-iodonaphthalene, 9,10-diiodoanthravene, 1,3-diiodobenzene, m-mothoxyiodobenzene, N-t-butoxycarbonyl-4-iodophenylalanine methyl ester, 4,4'-diiodobiphenyl, 1,4-diiodo-2-fluorobenzene, 2-iodopyridinbe, 2,7-diiodo-9,9-dinonylfluorene, vinylchloride, vinyl bromide, 1,2-dichloroethylene, allyl chloride, ally bromide, cyclohexen-1-yl-bromide, cyclopenten-1-yl-chloride, pyridine 2-trifluoromethanesulfonate, 1,1-bi-2-naphtholbis(trifluoromethanesulfonate), 1,2,2-trimethylvinyl trifluoromethanesulfonate, cyclohexen-1-yl trifluoromethanesulfonate, 4-bromophenyl trifluoromethanesulfonate, phenyldiazonium tetrafluoroborate and the like.

Examples of the substituted or unsubstituted aryl, heteroaryl group or alkenyl group represented by $R^2$ include, for example, the same groups as described above for the heteroaryl or alkenyl group represented by $R^1$.

Examples of the alkoxy group represented by $X^2$ include, for example, C1–10 alkoxy group such as methoxy or other groups, as exemplified above.

Examples of the compound of formula (3) wherein $X^2$ represents an alkylendioxy group or arylenedioxy group include a pinacol or catechol ester thereof.

Said boron compound of formula (3) maybe a cyclic anhydride (trimer) of formula (3'):

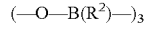

wherein $R^2$ is the same as defined above.

Preferred substituted or unsubstituted aryl group represented by $R^2$ include an aryl-boron compound of formula (5):

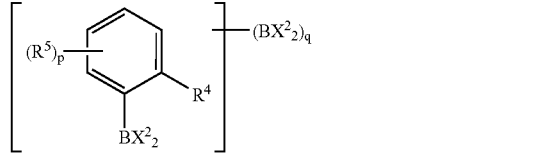

wherein $R^4$ represents a hydrogen atom, $X^2$ represents a hydroxy group, an alkoxy group, or the $X^2$ groups are bonded at their terminals to form an alkylenedioxy or arylenedioxy group, $R^5$ groups are the same or different and independently represent a substituent group as defined above, or $R^5$ groups on adjacent benzene carbon atoms, together with the benzene ring to which they are bonded, optionally form an ortho-fused, or ortho- and para-fused aromatic ring compound (e.g. naphthyl, anthracenyl, phenanthryl, indenyl, fluorenyl or pyrenyl group), and p represents an integer of 0 to 4, and q represents an integer of 0 or 1, or a cyclic anhydride trimer thereof.

Examples of the boron compound of formula (3) include, for example, phenylboronic acid, 2-methylphenylboronic acid, 3-methylphenylboronic acid, 4-methylphenylboronic acid, 2,3-dimethylphenylboronic acid, 2,4-dimethylphenylboronic acid, 2,5-dimethylphenylboronic acid, 2-ethylphenylboronic acid, 4-n-propylphenylboronic acid, 4-isopropylphenylboronic acid, 4-n-butylphenylboronicacid, 4-t-butylphenylboronic acid, 1-naphthylboronic acid, 2-naphthylboronic acid, 2-biphenylboronic acid, 3-biphenylboronic acid, 4-biphenylboronic acid, 2-fluoro-4-biphenylboronic acid, 2-fluorenylboronic acid, 9-fluorenylboronic acid, 9-phenathrenylboronic acid, 9-anthracenylboronic acid, 1-pyrenylboronic acid, 2-trifluoromethylphenylboronic acid, 3-trifluoromethylphenylboronic acid, 4-trifluoromethylphenylboronic acid, 3,5-bis(trifluoromethyl)phenylboronic acid, 2-methoxyphenylboronic acid, 3-methoxyphenylboronic acid, 4-methoxyphenylboronic acid, 2,5-dimethoxyphenylboronic acid, 4,5-dimethoxyphenylboronic acid, 2,4-dimethoxyphenylboronic acid, 2-ethoxyphenylboronic acid, 3-ethoxyphenylboronic acid, 4-ethoxyphenylboronic acid, 4-phenoxyboronic acid, 3,4-methylenedioxyphenylboronic acid, 2-fluorophenylboronic acid, 3-fluorophenylboronic acid, 4-fluorophenylboronic acid, 2,4-difluorophenylboronic acid, 2,5-difluorophenylboronic acid, 4,5-difluorophenylboronic acid, 3,5-difluorophenylboronic acid, 3,5-difluorophenylboronic acid, 2-formylphenylboronic acid, 3-formylphenylboronic acid, 4-formylphenylboronic acid, 3-formyl-4-methoxyphenylboronic acid, 2-cyanophenylboronic acid, 3-cyanophenylboronic acid, 4-cyanophenylboronic acid, 3-nitrophenylboronic acid, 3-acetylphenylboronic acid, 4-acetylphenylboronic acid, 3-trifluoroacetylphenylboronic acid, 4-trifluoroacetylphenylboronic acid, 4-methylthiophenylboronic acid, 4-biphenylphenylboronic acid, 3-carboxyphenylboronic acid, 4-carboxyphenylboronic acid, 4-carboxyphenylboronic acid, 3-aminophenylboronic acid, 2-(N,N'-dimethylamino)phenylboronic acid, 3-(N,N'-dimethylamino)phenylboronic acid, 4-(N,N'-dimethylamino)phenylboronic acid, 2-(N,N'-diethylamino)phenylboronic acid, 3-(N,N'-diethylamino)phenylboronic acid, 4-(N,N'-diethylamino)phenylboronic acid, 2-(N,N'-dimethylaminomethyl)phenylboronic acid, furane-2-boronic acid, dibenzofurane-4-boronic acid, benzofuran-2-boronic acid, thiophene-2-boronic acid, thiophene-3-boronic acid, 5-methylthiophene-2-boronic acid, 5-chlorothiophene-2-boronic acid, 4-methylthiophene-2-boronic acid, 2-acetylthiophene-2-boronic acid, benzothiophene-2-boronic acid, dibenzothlophene-4-boronic acid, pyridine-3-boronic acid, pyridine-4-boronic acid, pyrimidine-5-boronic acid, quinoline-8-boronic acid, isoquinoline-4-boronic acid, 1,4-benzenebis(boronic acid), phenylboronic acid pinacol ester, 4-cyanophenylboronic acid pinacol ester and the like.

The unsaturated organic compound (2) is reacted with the boron compound (3) usually in the presence of a base.

Examples of the base include, for example, an inorganic base such as hydroxide, carbonate, hydrogencarbonate, phosphate, carboxylate or alkoxide of an alkali metal or an alkaline earth metal. These base may be hydrate or anhydrous. Preferably used are hydroxide, carbonate, hydrogencarbonate, phosphate, or carboxylate of an alkali metal or an alkaline earth metal. More preferred are a carbonate or carboxylate of an alkali metal or an alkaline earth metal.

Examples of the inorganic base include, for example, lithium carbonate, sodium carbonate, potassium carbonate, cesium carbonate, calcium carbonate, barium carbonate, lithium phosphate, sodium phosphate, and potassium phosphate. More preferred are sodium carbonate, potassium carbonate, and potassium phosphate.

The base is usually used in an amount of 0.1 to 20 moles, preferably 1 to 5 moles per mol of the boron compound (3). The base may be used alone or as a mixture thereof.

The reaction is usually conducted in the presence of a solvent, preferably in an organic solvent. Water is also usable in the present reaction.

Examples of the organic solvent include, for example, an alcohol such as methanol, ethanol or the like, an aprotic polar solvent such as N-methylpyrolidone, N,N-dimethylformamide, N,N-dimethylacetamide, dimethylsulfoxide, acetonitrile or the like, an ether such as diethyl ether, diisopropyl ether, ethyleneglycol dimethyl ether, diethyleneglycol dimethyl ether, 1,4-dioxane, tetrahydrofuran, or the like, an aromatic hydrocarbon such as benzene, toluene, xylene, or the like, an aliphatic hydrocarbon such as hexane, heptane or the like, and a mixture thereof. The solvent is usually used in an amount of 1 part by weight to 200 parts by weight or less, preferably 5 parts by weight to 100 parts by weight or less per 1 part by weight of the unsaturated compound of formula (2).

The reaction is usually conducted at a temperature of 0° C. to 200° C. or less, preferably 20° C. to about 140° C.

The reaction is usually conducted under inert gas atmosphere such as nitrogen gas or argon gas and usually under normal pressure.

In the present process, the unsaturated organic compound (2), the boron compound (3), the nickel compound, the nitrogen-containing cyclic compound, and optionally the base and a suitable solvent are added to a reactor in an optional sequence and fashion. The reducing agent is added so as to prevent formation of undesirable reduced product of the unsaturated compound (2) and/or the boron compound (3), if necessary. For example, the catalyst composition produced by using the reducing agent is added to the reaction mixture of the unsaturated organic compound (2) and the boron compound (3) or vice versa.

After completion of the reaction, the produced coupling product is usually isolated by acidifying the reaction solution with a mineral acid such as a diluted hydrochloric acid, or diluted sulfuric acid, extracted with a suitable organic solvent, if desired, washing with water, distillation of the solvent. The product thus obtained may be further purified by distillation, recrystallization, various chromatographies, if necessary.

Examples of the coupling compound of formula (1) include a compound of formula (1a) to (1d), wherein $R^1$ and $R^2$ respectively correspond to the compound of formula (4) and the aryl-boron compound of formula (5).

Specific examples of the coupling product of formula (1) include, for example, biphenyl, 4-t-butylbiphenyl, 2-methoxybiphenyl, 4-t-butyl-3'-methylbiphenyl, 4-methoxybiphenyl, 4-formylbiphenyl, 3-methoxy-2'-methoxybiphenyl, ethyl 2-phenylphenylacetate, ethyl 3-phenylphenylacetate, ethyl 4-phenylphenylacetate, 3-nitrobiphenyl, 4-nitrobiphenyl, 9-phenylphenathrene, 1-benzyl-5-phenylterazole, 4-phenylacetophenone, 4-phenyl-N,N'-dimethylaniline, 2,4-difluorobiphenyl, 4-carboxybiphenyl, 1,4-diphenyl-2-fluorobenzene, 4-(4-trifluoromethylphenyl)phenol, 5-(3-methylphenyl)-2-methoxyaniline, 2-phenylbenzofurane, 4-(4-methoxybenzene)benzotrifluoride, 2-(3,5-difluorophenyl)naphthalene, 4-naphthylbenzamide, 9,10-diphenylanthracene, 9-(4-carboxyphenyl)-10-(3-methoxyphenyl)anthracene, 2-(2-ethoxyphenyl)fluorine, 4-(2,5-difluorophenyl)benzaldehyde, 4-(3-cyanophenyl)benzaldehyde, 1-vinyl-2,5-difluorobenzene, ethyl 4-(3-methylphenyl)phenylacetate, 2-(3-cyanophenyl)pyridine, 5-phenyl-1-methylimidazole, 2,5-dimethylbiphenyl, 2-methyl-2'-methylbiphenyl, 2-(3-(N,N'-dimethylamino)phenyl)toluene, 4-(2-ethoxyphenyl)benzamide, 2-pyridylbenzothiophene, 2-vinyl-5-methylthiophene, 5-(2-methylphenyl)uracil, 3-(4-acetylphenyl)toluene, 2-(4-acetylphenyl)thiophene, 2-(3-carboxyphenyl)toluene, 5-(4-methylphenyl)-2-methylbenzoxazole, 6-phenyl-2-methylpurine, 5-(3-furyl)uridine, 2-(3-nitrophenyl)toluene, 2-(4-cyanophenyl)toluene, 2-(2-methylphenyl)benzimidazole, 3-(1-phenyl-1H-tetrazole)thiophene, 2-(2,4-dimethylphenyl)benzylcyanide, 2-fluoro-2', 6'-dimethylbiphenyl, 3-carboxy-2', 6'-dimethylbiphenyl, 3-biphenyl-2', 6'-dimethylbiphenyl and the like.

EXAMPLES

The present invention will be further illustrated by way of Examples, but are not to be construed to limit the invention thereto. In the following Tables and Examples, the reaction mixture was analyzed by gas-chromatography and the results are shown by the respective chromatogram peak area ratio (%) of the product, byproduct(s), and the unreacted unsaturated organic compound of formula (1) to the total peak area thereof.

Example 1

Under argon atmosphere, 0.4 mmol (61 mg) of p-methoxyphenylboronic acid, 0.3 mmol (5 mg) of 3-chlorotoluene, 1.13 mmol (240 mg) of potassium phosphate, 0.030 mmol (4.6 mg) of 1,8-diazabicyclo[5.4.0]-7-undecene and 0.015 mmol (4.1 mg) of bis(1,5-cyclooctadiene)nickel were added to 1 ml of dioxane in a reaction vessel. The resulting reaction solution was warmed to a temperature of 80° C., and was stirred for 3 hours at the same temperature. After completion of the reaction, the reaction mixture was left standing at room temperature, 10 ml of 1N hydrochloric acid were added thereto to dissolve potassium phosphate. The resulting mixture was transferred to a separatory funnel, extracted with ethyl acetate, and the separated organic phase was washed with saturated aqueous sodium chloride solution. The obtained desired product of the reaction, 4-methoxy-3'-methylbiphenyl showed 99% peak area, and a byproduct, 3,3'-dimethylbiphenyl showed 1% peak area in the chromatogram. Conversion of 3-chlorotoluene was 100%, which means that the unreacted 3-chlorotoluene showed 0%.

Example 2 to 12

In Examples 2 to 11, 0.030 mmol of the nitrogen-containing cyclic compounds shown in Table 1 were used respectively in place of 1,8-diazabicyclo[5.4.0]-7-undecene used in Example 1 and the reactions were conducted in a similar manner as in Example 1.

In Examples 7 and 11, the figures shown in the parenthesis are the result obtained by using 0.5 ml of tetrahydrofuran in place of dioxane and the reactions were conducted for 8 hours in place of 3 hours in Example 1.

In Example 10, the figures shown in the parenthesis are the results obtained by using 1 ml of ethyleneglycol dimethy ether was used in place of dioxane and the reaction temperature was set at 100° C. in place of 80° C. and the reaction was continued for 8 hours in place of 3 hours in Example 1.

In Examples 8 and 9, 0.060 mmol of the nitrogen-containing cyclic compounds listed in Table 1 were used.

Comparative Example 1

The reaction was conducted in a similar manner as in Example 1 except that 0.030 mmol (8.4 mg) of triethylamine was used in place of 1,8-diazabicyclo[5.4.0]-7-undecene. The results are summarized in Table 2 below.

Comparative Example 2

The reaction was conducted in a similar manner as in Example 1 except that 0.015 mmol (2.3 mg) of 2,2'-bipyridyl was used in place of 1,8-diazabicyclo[5.4.0]-7-undecene. The results are summarized in Table 2 below.

TABLE 1

| Example No | Nitrogen-containing cyclic compound Formula | pKa | Reaction Results (%) Coupling Compound | Residual ratio | By-product |
|---|---|---|---|---|---|
| 1 | (structure) | 12.8 | 99 | 0 | 1 |
| 2 | (structure) | 13.1 | 73 | 25 | 2 |
| 3 | (structure) | 9.7 | 98 | 1 | 1 |
| 4 | (structure) | 8.6 | 71 | 28 | 2 |
| 5 | (structure) | 7.0 | 98 | 2 | 0 |
| 6 | (structure) | 5.7 | 78 | 21 | 1 |
| 7 | (structure) | 7.8 | 88 | 10 | 2 |
| 8 | (structure) | 5.4 | 50 (76) | 49 (24) | 0 (0) |
| 9 | (structure) | 5.0 | 52 (69) | 48 (31) | 0 (0) |
| 10 | (structure) | 3.4 | 45 (64) | 50 (36) | 5 (0) |
| 11 | (structure) | 3.0 | 49 (74) | 48 (25) | 3 (1) |
| 12 | (structure) | −1.7 | 54 (81) | 46 (17) | 0 (2) |

TABLE 2

| Comparative Example No | Nitrogen-containing cyclic compound Formula | pKa | Reaction Results (%) Coupling Compound | Residual ratio | By-product |
|---|---|---|---|---|---|
| 1 | (structure) | 10.7 | 38 | 62 | 0 |
| 2 | (structure) | 4.3 | 54 | 23 | 23 |

Experiments 1 to 9

The reactions were conducted in a similar manner as in Example 1 except that 0.030 mmol of each of the nitrogen-containing cyclic compound as listed in Table 3 below was used in place of 1,8-diazabicyclo[5.4.0]-7-undecene in Experiments 1 to 3 and 5 to 9, and 0.015 mmol of the listed compound was used in Experiment 4. The results are summarized in Table 3 below.

TABLE 3

| Exp. No | Nitrogen-containing cyclic compound Formula | pKa | Coupling Compound | Residual ratio | Byproduct |
|---|---|---|---|---|---|
| 1 | 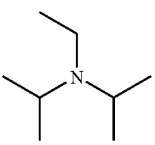 | 10.2 | 6 | 94 | 0 |
| 2 | 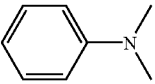 | 5.1 | 9 | 91 | 0 |
| 3 | 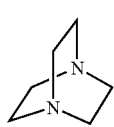 | 8.2 | 26 | 74 | 0 |
| 4 | 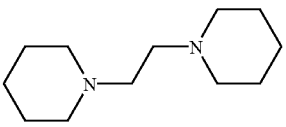 | 9.0 | 11 | 89 | 0 |
| 5 | 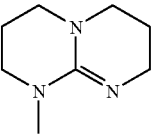 | 15.0 | 3 | 97 | 0 |
| 6 | 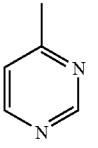 | 2.0 | 23 | 77 | 0 |
| 7 | 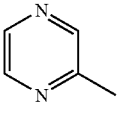 | 1.3 | 12 | 84 | 4 |
| 8 | 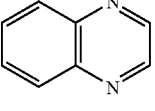 | 0.6 | 7 | 87 | 6 |
| 9 | 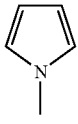 | −2.8 | 23 | 77 | 0 |

Exp. 10

The reaction was conducted in a similar manner as in Example 1 except that 0.0075 mmol (6.9 mg) of trisdibenzylideneacetone palladium was used in place of 1,5-cyclooctadiene)nickel. Gaschromatography analysis showed following results: 4-Methoxy-3'-methylbiphenyl: 0%, 3-methyl-3'-methylbiphenyl: 0%, unreacted 3-chlorotoluene: 100%.

Example 13

The reaction was conducted in a similar manner as in Example 1 except that 0.4 mmol (60 mg) of 2,5-dimethylphenylboronic acid was used in place of p-methoxyphenylboronic acid and 0.030 mmol (2.5 mg) of N-methylimidazole was used in place of 1,8-diazabicyclo[5.4.0]-7-undecene. The gaschromatography analysis of the reaction mixture showed that 3-methyl-2',5'-dimethylbiphenyl: 99%, byproduct 3,3'-dimethylbiphenyl: 0%, and unreacted 3-chlorotoluene: 1%.

Example 14

The reaction was conducted in a similar manner as in Example 1 except that 0.4 mmol (60 mg) of 2,5-dimethylphenylboronic acid was used in place of p-methoxyphenylboronic acid and 0.03 mmol (38 mg) of 2-chlorotoluene was used in place of 3-chlorotoluene. The gaschromatography analysis of the reaction mixture showed that 2-methyl-2',5'-dimethylbiphenyl: 83%, byproduct 2,5'-dimethyl-2',5'-dimethylbiphenyl: 3%, and unreacted 2-chlorotoluene: 14%.

Examples 15 to 33

The reactions were conducted in a similar manner as in Example 1 except that 0.4 mmol of the boron compound as listed in Table 4 below was used in place of p-methoxyphenylboronic acid, 0.015 mmol (2.5 mg) of N-methylimidazole was used in palace of 1,8-diazabicyclo[5.4.0]-7-undecene, 0.3 mmol of unsaturated organic compounds as listed in Table 4 were used in place of 3-chlorotoluene, and 0.57 mmol (120 mg) of potassium phosphate was used. In addition, 1 ml of tetrahydrofuran was used in place of dioxane in Examples 16 to 23 and 27 to 33, 1 ml of ethyleneglycol dimethyl ether was used in place of dioxane in Examples 15 and 24 to 26, the reaction was continued for 3 hours in Examples 16 to 23 and 27 to 33, and the reaction continued for 5 hours in Examples 15 and 24 to 26.

The figures in the parenthesis are obtained by gaschromatography analysis using Internal Standard.

TABLE 4

| Example No | Compound (2) | Compound (3) | Reaction Results (%) | | |
|---|---|---|---|---|---|
| | | | Coupling Compound | Residual ratio | Byproduct |
| 15 | Cl—⟨C6H4⟩—CN | (HO)₂B—⟨C6H4⟩—CH₃ | 91 | 9 | 0 |
| 16 | Cl—⟨C6H4⟩—CF₃ | " | 91 | 7 | 2 |
| 17 | Cl—⟨C6H4⟩—F | " | 99 | 0 | 1 |
| 18 | Cl—⟨C6H4⟩—CO₂Me | " | 100 (100) | 0 | 0 |
| 19 | Cl—⟨C6H4⟩—COCH₃ | " | 94 | 6 | 0 |
| 20 | Cl—⟨C6H4⟩—OCH₃ | " | 98 (99) | 0 (0) | 2 (1) |
| 21 | 2-NC-C6H4-Cl | " | 93 | 7 | 0 |

TABLE 4-continued

| Example No | Compound (2) | Compound (3) | Coupling Compound | Residual ratio | Byproduct |
|---|---|---|---|---|---|
| 22 | 2-chlorotoluene | (HO)₂B–C₆H₄–OCH₃ (para) | 99 | 1 | 0 |
| 23 | 4-bromobenzonitrile | (HO)₂B–C₆H₄–CH₃ (para) | 100 | 0 | 0 |
| 24 | 4-chlorotoluene | (HO)₂B–C₆H₄–CO₂Me (para) | 92 | 1 | 9 |
| 25 | " | (HO)₂B–C₆H₄–COCH₃ (para) | 92 | 6 | 1 |
| 26 | " | (HO)₂B–C₆H₄–CF₃ (para) | 92 (92) | 0 (0) | 8 (8) |
| 27 | " | (HO)₂B–C₆H₄–OCH₃ (para) | 93 | 4 | 2 |
| 28 | " | (HO)₂B–C₆H₄–N(CH₃)₂ (para) | 62 | 38 | 0 |
| 29 | 4-chlorotoluene | trans-styryl-B(OH)₂ | 89 (88) | 0 | 11 |
| 30 | iodobenzene | thiophen-3-yl-B(OH)₂ | 43 | 57 | 0 |
| 31 | " | benzofuran-2-yl-B(OH)₂ | 74 | 26 | 0 |
| 32 | 2-bromo-3-methylcyclopent-2-enone | (HO)₂B–C₆H₄–OCH₃ (para) | 68 | 32 | 0 |
| 33 | 4-methylphenyl phenyl sulfonate (tosylate) | " | 72 | 29 | 0 |

Examples 34 to 40

The reactions were conducted in a similar manner as in Example 1 except that 0.015 mol of the nitrogen-containing cyclic compound were used in place of 1,8-diazabicyclo[5.4.0]-7-undecene, 0.45 mmol of the listed base as used in place of potassium phosphate, and 1 ml of the listed solvents were respectively used in place of dioxane.

TABLE 5

| Example No | Nitrogen-containing cyclic compound | Base | Solvent | Coupling Compound | Residual ratio | By-product |
|---|---|---|---|---|---|---|
| 34 | N-methyl-imidazole | Potassium phosphate trihydrate | Dioxane | 72 | 26 | 2 |
| 35 | N-methyl-imidazole | Potassium phosphate trihydrate | Tetrahydrofuran | 98 | 0 | 2 |
| 36 | N-methyl-imidazole | Potassium phosphate trihydrate | Ethyleneglycol dimethyl ether | 85 | 10 | 5 |
| 37 | N-methyl-imidazole | Potassium phosphate trihydrate | Toluene | 57 | 41 | 2 |
| 38 | N-methyl-imidazole | Potassium carbonate | Tetrahydrofuran | 83 | 17 | 0 |
| 39 | 1,8-Diazabicyclo[5,4.0]-7-undecene | Potassium carbonate | Ethyleneglycol dimethyl ether | 43 | 57 | 0 |
| 40 | N,N-Dimethyaminopyridine | Potassium carbonate | Tetrahydrofuran | 54 | 46 | 0 |

Example 41

The reaction was conducted in a similar manner as in Example 1 except that 0.015 mmol (16 mg) of N,N-dimethylaminopyridine (supported on polystyrene) was used in place of 1,8-diazabicyclo[5.4.0]-7-undecene, 4-chlorotoluene was used in place of 3-chlorotoluene, 0.57 mmol (120 mg) of potassium phosphate was used, and 1 ml of tetrahydrofuran was used in place of dioxane. The reaction results showed following results: 4-methoxy-4'-methylbiphenyl (desired product): 37%, 4,4'-dimethylbiphenyl (byproduct): 0%, and unreacted 4-chlorotoluene: 63%.

Example 42

The reaction was conducted in a similar manner as in Example 1 except that 0.8 mmol (98 mg) of phenylboronic acid was used place of p-methoxyphenylboronic acid, and 0.015 mmol (2.5 mg) of N-methylimidazole was used in place of 1,8-diazabicyclo[5.4.0]-7-undecene, 0.3 mmol (74 mg) of 9,10-dichloroanthracene was used in place of 3-chlorotoluene, 1.14 mmol (240 mg) of potassium phosphate was used, 1 ml of ethyleneglycol dimethyl ether was used in place of dioxane, and the reaction was continued for 5 hours. The reaction result showed that 9,10-diphenylanthracene: 100%, and 9,10-dichloroanthracene: 0%.

Example 43

The reaction was conducted in a similar manner as in Example 1 except that 0.015 mmol (2.5 mg) of N-methylimidazole was used in place of 1,8-diazabicyclo[5.4.0]-7-undecene, 0.3 mmol (57 mg) of 3-bromochlorobenzene was used in place of 3-chlorotoluene, 0.57 mmol (120 mg) of potassium phosphate was used, 1 ml of tetrahydrofuran was used in place of dioxane, and reaction was continued for 1 hour. The reaction results showed following results: 1,4-di(4-methoxyphenyl)biphenyl (desired product): 100%, and unreacted 3-bromochlorobenzene: 0%.

Example 44

The reaction was conducted in a similar manner as in Example 1 except that 0.4 mmol (62 mg) of 2,7-(9,9'-di-n-octylfluorenyl)diboronic acid was used place of p-methoxyphenylboronic acid, and 0.015 mmol (2.5 mg) of N-methylimidazole was used in place of 1,8-diazabicyclo[5.4.0]-7-undecene, 0.3 mmol (41 mg) of potassium carbonate was used in place of potassium phosphate was used, 1 ml of tetrahydrofuran was used in place of dioxane, and the reaction was continued for 5 hours. The reaction result showed that 2,7-di(3-methylphenyl)-9,9'-di-n-octylfluorene: 88% in terms of 3-chlorotoluene.

Example 45

The reaction was conducted in a similar manner as in Example 1 except that 0.4 mmol (69 mg) of 2-naphthylboronic acid was used in place of p-methoxyphenylboronic acid, 0.015 mmol (2.5 mg) of N-methylimidazole was used in place of 1,8-diazabicyclo[5.4.0]-7-undecene, 0.3 mmol (34 mg) of 2-chloropyridine was used in place of 3-chlorotoluene, and 1 ml of tetrahydrofuran was used in place of dioxane. The reaction results showed following results: 2-(2-naphthyl)pyridine: 41%, 2-pyridylpyridine: 0% and unreacted 2-chloropyridine: 59%.

Example 46

0.015 Mmol (4.4 mg) of dichlrorobis(N-methylimidazole) nickel was mixed with 0.3 ml of dioxane under argon atmosphere and stirred, then 0.03 mmol (0.019 ml) of n-butyl lithium (1.59M hexane solution) was added thereto and stirred at room temperature for 10 minutes to obtain catalyst preparation solution. To a solution of 0.4 mmol (49 mg) of phenylboronic acid, 0.3 mmol (56 mg) of 4-cyano-bromobenzene, and 0.57 mmol (120 mg) of potassium phosphate in 0.7 ml of dioxane was added the catalyst preparation solution, then the resulting mixture was heated to 80° C., and stirred at the temperature for 5 hours. After completion of the reaction, the mixture was left standing at room temperature, 10 ml of 1N hydrochloric acid was added thereto to dissolve excess of potassium phosphate. The mixture was transferred to a separatory funnel and extracted with ethyl acetate, and the separated organic phase was washed with saturated aqueous sodium chloride solution. Desired 4-cyanobiphenyl: 92%, byprodyct, 4,4'-dicyanobi-phenyl: 0%, and unreacted 4-cyanobromobenzene: 8%.

Example 47

0.4 Mmol (60 mg) of 2,5-dimethylphenylboronic acid, 0.3 mmol (38 mg) of 2-chlorotoluene, 0.57 mmol (120 mg) of potassium phosphate, 0.015 mol (4.4 mg) of dichlrorobis (N-methylimidazole)nickel was mixed with 1 ml of tetrahydrofuran under argon atmosphere and stirred. Then the resulting mixture was heated to 80° C., and stirred at the temperature for 3 hours. After completion of the reaction, the mixture was left standing at room temperature, 10 ml of 1N hydrochloric acid was added thereto to dissolve excess of potassium phosphate. The mixture was transferred to a separatory funnel and extracted with ethyl acetate, and the separated organic phase was washed with saturated aqueous sodium chloride solution. Desired 2-methyl-2',5'-dimethyl-biphenyl: 51%, byprodyct, 2,5-dimethyl-2',5'-dimethylbi-phenyl: 0%, and unreacted 2-chlorotoluene: 49%.

Example 48

The reaction was conducted in a similar manner as in Example 1 except that 0.015 mmol (2.5 mg) of N-methylimidazole was used in place of 1,8-diazabicyclo[5.4.0]-7-undecene, 0.3 mmol (38 mg) of 4-chlorotoluene was used in place of 3-chlorotoluene, 0.57 mmol (120 mg) of potassium phosphate was used, 0.015 mmol (4.4 mg) of nickel chloride hexahydrate was used in place of bis(1,5-cyclooctadiene) nickel, and 1 ml of tetrahydrofuran was used in place of dioxane. Gaschromatography analysis of the reaction mixture showed that 4-methoxy-4'-methylbiphenyl: 95%, byproduct 4,4'-dimethylbiphenyl: 2%, and unreacted 4-chlorotoluene: 3%.

TABLE 6

| Example | Compound (2) | Compound (3) | Coupling Product |
|---|---|---|---|
| 41 | Cl—⟨phenyl⟩—CH3 | (HO)2B—⟨phenyl⟩—OCH3 | CH3—⟨phenyl⟩—⟨phenyl⟩—OCH3 |
| 42 | 9,10-dichloroanthracene | (HO)2B—⟨phenyl⟩ | 9,10-diphenylanthracene |
| 43 | 3-bromo-1-chlorobenzene (Br, Cl on phenyl) | (HO)2B—⟨phenyl⟩—OCH3 | terphenyl with two OCH3 groups |
| 44 | 3-methyl-1-chlorobenzene | (HO)2B—⟨9,9-dioctylfluorene⟩—B(OH)2 | 2,7-bis(3-methylphenyl)-9,9-dioctylfluorene |

TABLE 6-continued

| Example | Compound (2) | Compound (3) | Coupling Product |
|---|---|---|---|
| 45 | 2-chloropyridine | 2-naphthylboronic acid | 2-(2-naphthyl)pyridine |
| 46 | 4-bromobenzonitrile | phenylboronic acid | 4-cyanobiphenyl |
| 47 | 2-chlorotoluene | 2,5-dimethylphenylboronic acid | 2,2',5'-trimethylbiphenyl |
| 48 | 4-chlorotoluene | 4-methoxyphenylboronic acid | 4-methoxy-4'-methylbiphenyl |

Example 49 and 50

The reactions were conducted in a similar manner as in Example 48 except that 0.015 mmol of nickel compounds as listed in Table 7 was used, and the results are summarized in Table 7.

TABLE 7

| | | Reaction Results (%) | | |
|---|---|---|---|---|
| Example No | Nickel compound | Coupling Compound | Residual ratio | Byproduct |
| 49 | Nickel Nitrate hexahydrate | 85 | 15 | 0 |
| 50 | Nickel acetate tetrahydrate | 72 | 26 | 1 |

Example 51

0.015 mmol (2.5 mg) of N-methylimidazole, 0.015 mmol (4.4 mg) were mixed in 0.3 ml of ethyleneglycol dimethyl ether under argon atmosphere and stirred for 10 minutes to obtain a catalyst preparation solution.

Ethyleneglycol dimethyl ether was removed to give a solid material. IR spectrum of the obtained product showed a characteristic absorbance at 1611 cm$^{-1}$.

Experiments are conducted in a similar manner as in Example 1 to produce the desired coupling product with the exception that the catalyst preparation solution and the solid material respectively are used.

What is claimed is:

1. A process for producing a coupling compound of formula (1):

$$(Y-)_{(n-1)}R^1-R^2-(R^1)_{(n'-1)} \quad (1),$$

wherein $R^1$ and $R^2$ independently represent
a substituted or unsubstituted aryl group,
a substituted or unsubstituted heteroaryl group, or
a substituted or unsubstituted linear, branched or cyclic alkenyl group,
n and n' independently represent an integer of 1 or 2, provided that n and n' do not simultaneously represent 2, and when n=2, Y represents $R^2$, or $X^1$ as defined below,
which process comprises reacting
an unsaturated organic compound of formula (2):

$$n'(R^1X^1_n) \quad (2)$$

wherein n, n', and $R^1$ are the same as defined above, and $X^1$ is the same or different and independently represents a leaving group and is bonded with a sp2 carbon atom of $R^1$ group,
with a boron compound of formula (3);

$$m\{R^2(BX^2_2)_{n'}\} \quad (3)$$

wherein $R^2$ and n' are the same as defined above,
$X^2$ represents a hydroxy group, an alkoxy group, or $X^2$ groups are bonded at their terminals to form an alkylenedioxy group or an arylenedioxy group, and
m represents an integer of 1 or 2, provided that the boron atom is bonded with a sp2 carbon atom of R² group, and m≦n, wherein n is the same as defined in connection with formula (1) above, or a cyclic anhydride trimer thereof of formula: (—O—B(R²)—)₃, wherein R² is the same as defined above, in the presence of a catalyst comprising (A) a nickel compound, and (B) a nitrogen-containing cyclic compound selected from the group consisting of:

(a) a nitrogen-containing cyclic compound of formula (I):

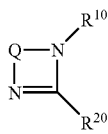

wherein Q represents a substituted or unsubstituted alkylene group, a substituted or unsubstituted alkenylene group, a substituted or unsubstituted 1,2-phenylene group, a substituted or unsubstituted 1,8-naphthylene group, or —N=N— group, R¹⁰ represents a substituted or unsubstituted hydrocarbon group, and R²⁰ represents a hydrogen atom, a substituted or unsubstituted hydrocarbon group, alternatively, R¹⁰ and R²⁰ are bonded at their terminals to form a substituted or unsubstituted alkylene, or alkenylene group, (b) a substituted or unsubstituted pyridine or fused ring compound thereof of which conjugated acid has pKa of 5 or more, (c) a substituted pyrimidine or substituted or unsubstituted fused pyrimidine compound of which conjugate acid has pKa of 3 or more, (d) an enamine compound obtainable from a cyclic ketone compound and a cyclic secondary amine compound, (e) a substituted or unsubstituted 2H-pyrrole, 3,4-dihydro-2H-pyrrole or 3H-pyrrole or fused ring compound thereof, or (f) a substituted or unsubstituted N-hydrocarbyl 1,2,3-triazole, or a fused ring compound thereof.

2. A process according to claim 1, wherein the leaving group is a halogen atom, a sulfonate group, or a diazonium salt.

3. A process according to claim 1, wherein the nitrogen-containing cyclic compound is the nitrogen-containing cyclic compound of formula (I).

4. A process according to claim 3, wherein Q is the unsubstituted alkylene group.

5. A process according to claim 3, wherein Q is the unsubstituted alkenylene group.

6. A process according to claim 3, wherein Q is the substituted or unsubstituted 1,2-phenylene group.

7. A process according to claim 3, wherein Q is —N=N—.

8. A process according to claim 1, wherein the nitrogen-containing cyclic compound is the substituted or unsubstituted pyridine or fused ring compound thereof of which conjugated acid has pKa of 5 or more.

9. A process according to claim 1, wherein the nitrogen-containing cyclic compound is the substituted pyrimidine or substituted or unsubstituted fused pyrimidine compound of which conjugate acid has pKa of 3 or more.

10. A process according to claim 1, wherein the nitrogen-containing cyclic compound is the enamine compound obtainable from a cyclic ketone compound and a cyclic secondary amine compound.

11. A process according to claim 1, wherein the nitrogen-containing cyclic compound is the substituted or unsubstituted 2H-pyrrole, 3,4-dihydro-2H-pyrrole or 3H-pyrrole or fused ring compound thereof.

12. A process according to claim 1, wherein the nitrogen-containing cyclic compound is the substituted or unsubstituted N-hydrocarbyl-1,2,3-triazole or fused ring compound thereof.

13. A process according to any one of claims 1 to 8, wherein the nickel compound is nickel(II) chloride, nickel (II) bromide, nickel(II) iodide, nickel(II) nitrate, bis(1,5-cyclooctadiene)nickel, or nickel(II) acetate.

14. A process according to claim 1, wherein the nitrogen-containing cyclic compound is N-methylimidazole, N,N-dimethylaminopyridine, or 1,8-diazabicyclo[5.4.0]-7-undecene.

15. A process according to claim 1, wherein the catalyst is dichlorobis(N-methylimidazole)nickel.

16. A process according to claim 1, wherein the unsaturated organic compound of formula (2) is a compound of formula (4):

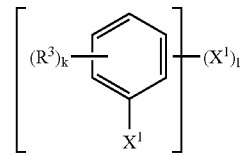

(4)

wherein R³ is the same or different and each independently represents a substituent group, or R³ groups on adjacent benzene carbon atoms, together with the benzene ring to which they are bonded, form an ortho-fused, or ortho- and peri-fused aromatic ring compound, X¹ represents a leaving group bonded with a sp2 carbon atom, l is an integer of 0 or 1, and k is an integer of 0 to 5, provided that at least one ortho-position of the leaving group is a hydrogen atom or a common carbon atom of the fused aromatic ring compound.

17. A process according to claim 1, wherein the boron-compound of formula (3) is a compound of formula (5):

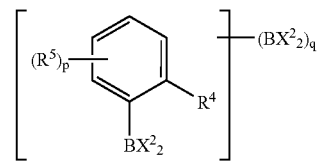

(5)

wherein R⁴ represents a hydrogen atom, $X^2$ represents a hydroxy group, an alkoxy group, or the $X^2$ groups are bonded at their terminals to form an alkylenedioxy or arylenedioxy group, $R^5$ groups are the same or different and independently represent a substituent group, or $R^5$ groups on adjacent benzene carbon atoms, together with the benzene ring to which they are bonded, optionally form an ortho-fused, or ortho- and peri-fused aromatic ring compound, and p represents an integer of 0 to 4, and q represents an integer of 0 or 1, or a cyclic anhydride trimer thereof.

18. A process according to claim 1, which comprises reacting the unsaturated organic compound of formula (2) with the boron compound of formula (3) in the presence of the nitrogen containing cyclic compound as defined in (B) and the nickel compound in (A) as catalyst components.

* * * * *